United States Patent
Yuyama et al.

(10) Patent No.: US 6,774,131 B1
(45) Date of Patent: Aug. 10, 2004

(54) REMEDIES FOR ENDOTHELIN-INDUCED DISEASES

(75) Inventors: Hironori Yuyama, Tsukuba (JP); Akira Fujimori, Tsukuba (JP); Masanao Sanagi, Tsukuba (JP); Hironori Harada, Tsukuba (JP); Akiko Koakutsu, Tsukuba (JP); Mikiko Mori, Tsukuba (JP); Nobuyuki Yamamoto, Tokyo (JP)

(73) Assignee: Yamanouchi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/181,489

(22) PCT Filed: Oct. 27, 2000

(86) PCT No.: PCT/JP00/07573

§ 371 (c)(1),
(2), (4) Date: Jul. 19, 2002

(87) PCT Pub. No.: WO01/60370

PCT Pub. Date: Aug. 23, 2001

(30) Foreign Application Priority Data

Feb. 16, 2000 (JP) ................................ 2000-037313
Feb. 16, 2000 (JP) ................................ 2000-037314

(51) Int. Cl.[7] .................. A61K 31/505; A61K 31/506; A61K 31/513

(52) U.S. Cl. .................. 514/269; 514/816; 514/817; 514/818; 514/825; 514/883; 514/908

(58) Field of Search ................... 514/269, 816–818, 514/825, 883, 908

(56) References Cited

U.S. PATENT DOCUMENTS 6,030,975 A * 2/2000 Romerdahl ................ 514/274
6,083,955 A   7/2000 Harada et al. ............. 514/269

FOREIGN PATENT DOCUMENTS

WO  WO 98/41206   9/1998  ......... A61K/31/505
WO  wo 99/56761  11/1999  ......... A61K/38/00

OTHER PUBLICATIONS

Verhaar et al., Abstract No. 219 (P40), "Pharmacokinetic and Pharmacodynamic Effects of ABT–627, an Oral $ET_A$ Selective Endothelin Antagonist in Humans," Program and Abstracts, Sixth International Conference on Endothelin, Oct. 10–13, 1999.

Brothman et al., Phenotypic and Cytogenetic Characterization of a Cell Line Derived from Primary Prostatic Carcinoma, *Int. J. Cancer*, 44: 898–903, 1989.

Carducci et al., Phase I Clinical Results of ABT–627, an Endothelin Receptor Antagonist, for Refractory Adenocarcinomas, *Proceedings of the American Association for Cancer Research*, 40: 91, Abstract No. 601, 1999.

Carducci et al., Endothelin Receptor Antagonist, ABT–627, for Prostate Cancer: Initial Trial Results, *The Journal of Urology*, 161: 176, Abstract No. 679, 1999.

Carducci et al., A Placebo (PBO) Controlled Phase II Dose–Ranging Evaluation of an Endothelin–A Receptor Antagonist for Men with Hormone Refractory Prostate Cancer (HRPCa) and Disease–Related Pain, *Proceedings of ASCO*, vol. 19 (2000) No. 1314.

Dahlöf et al., Regional Haemodynamic Effects of Endothelin–1 in Rat and Man: Unexpected Adverse Reactions, *Journal of Hypertension*, 8: 811–817, 1990.

Nelson et al., Identification of Endothelin–1 in the Pathophysiology of Metastatic Adenocarcinoma of the Prostate, *Nature Medicine*, 1: 944–949, 1995.

Nelson et al., Endothelin–1 Production and Decreased Endothelin B Receptor Expression in Advanced Prostate Cancer[1], *Cancer Research*, 56: 663–668, 1996.

Piovezan et al., Endothelins Potentiate Formalin–Induced Nociception and Paw Edema in Mice, *Can. J. Physiol. Pharmacol.*, 75: 596–600, 1997.

Raffa et al., Endothelin–Induced Nociception in Mice: Mediation by $ET_A$ and $ET_B$ Receptors, *The Journal of Pharmacology and Experimental Therapeutics*, 276: 647–651, 1996.

Scher et al., Bone Metastases: Improving the Therapeutic Index, *Seminars in Oncology*, 21: 630–656, 1994.

Shibata et al., Modified Formalin Test: Characteristic Biphasic Pain Response, *Pain*, 38: 347–352, 1989.

Sudo et al., In Vitro Differentiation and Calcification in a New Clonal Osteogenic Cell Line Derived from Newborn Mouse Calvaria, *The Journal of Cell Biology*, 96: 191–198, 1983.

Suzuki et al., $ET_A$ Receptor Mediates the Signaling of Endothelin–1 in Osteoblast–Like Cells, *Bone*, 21: 143–146, 1997.

Takuwa et al., Endothelin–1 Activates Phospholipase C and Mobilizes $Ca^{2+}$ from Extra– and Intracellular Pools in Osteoblastic Cells, *American Journal of Physiology*, 257: E797–E803, 1989.

Takuwa et al., The Effects of the Endothelin Family Peptides on Cultured Osteoblastic Cells from Rat Calvariae, *Biochemical and Biophysical Research Communications*, 170: 998–1005, 1990.

* cited by examiner

Primary Examiner—John Pak
(74) Attorney, Agent, or Firm—Finnegan, Henderson, Farabow, Garrett & Dunner, L.L.P.

(57) ABSTRACT

A pharmaceutical composition for therapeutically treating prostate cancer, the pharmaceutical composition containing N-[6-methoxy-5-(2-methoxyphenoxy)-2-(2-pyrimidinyl)-4-pyrimidinyl]-2-phenylethenesulfoneamide or a pharmaceutically acceptable salt thereof as the effective component.

7 Claims, 3 Drawing Sheets

Fig.1

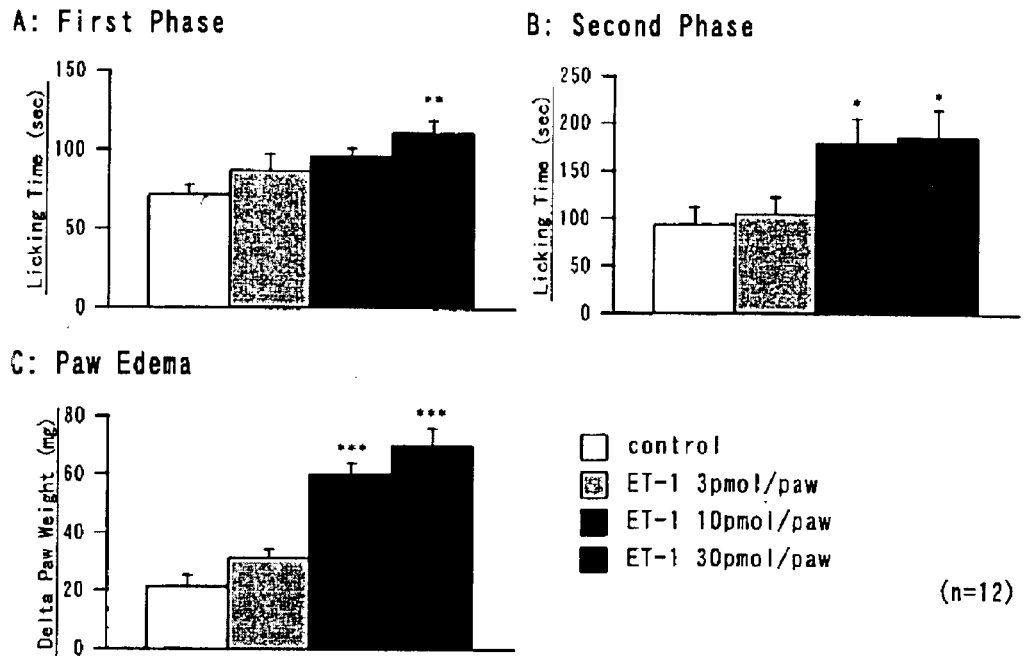

A: First Phase
B: Second Phase
C: Paw Edema

☐ control
▨ ET-1 3pmol/paw
■ ET-1 10pmol/paw
■ ET-1 30pmol/paw (n=12)

*$P<0.05$, $P<0.01$, *$P<0.001$, significantly different from control (One-way ANOVA followed by Dunnett's Multiple Range test)

Fig.2

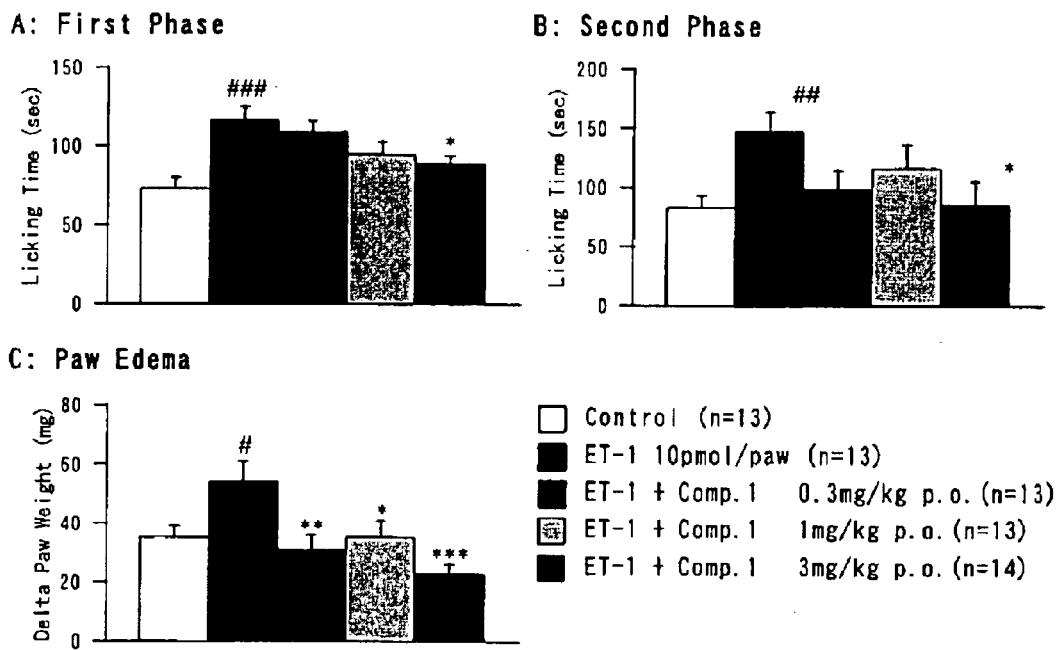

A: First Phase
B: Second Phase
C: Paw Edema

☐ Control (n=13)
■ ET-1 10pmol/paw (n=13)
■ ET-1 + Comp. 1  0.3mg/kg p.o. (n=13)
▨ ET-1 + Comp. 1  1mg/kg p.o. (n=13)
■ ET-1 + Comp. 1  3mg/kg p.o. (n=14)

$P<0.05$, ##$P<0.01$, ###$P<0.001$, significantly different from control (Un paired t- test).
*$P<0.05$, $P<0.01$, *$P<0.001$, significantly different from ET-1 One-way ANOVA followed by Dunnet's Multiple Range test).

*; P<0.05, ; P<0.01, *; P<0.001 vs corresponding Cont. values

; P<0.001 vs ET-1 (0.1 nM) values by Dunnett multiple range test

REMEDIES FOR ENDOTHELIN-INDUCED DISEASES

This application is a 371 of PCT/JP00/07573, filed on Oct. 27, 2000.

TECHNICAL FIELD

The present invention relates to a pharmaceutical drug; more specifically, the invention relates to a therapeutic agent for reducing pain in an endothelin-induced disease, such as prostate cancer; a therapeutic agent for ameliorating osteogenic disorders and/or a therapeutic agent for reducing pain involved in osteogenesis; a therapeutic agent for reducing pain involved in the bone metastasis of prostate cancer and/or a therapeutic agent for ameliorating osteogenic disorders due to the bone metastasis of prostate cancer; a therapeutic agent for suppressing the growth of the cancer cell of prostate cancer; or a therapeutic agent for suppressing the progress of prostate cancer.

BACKGROUND OF THE INVENTION

N-[6-Methoxy-5-(2-methoxyphenoxy)-2-(2-pyrimidinyl)-4-pyrimidinyl]-2-phenylethenesulfoneamide or a salt thereof is described in the International Patent Publication No. 97/22595. The actions thereof to suppress ET-1 binding to endothelin ETA receptor and to suppress ET-1 induced vascular constriction and blood pressure elevation are disclosed therein, indicating that the compound or a salt thereof can be used for treating various diseases primarily including cardiovascular diseases, for which endothelin is responsible.

For the purpose of creating a new therapeutic agent, the present inventors have made more detailed investigations about a possibility of the application of N-[6-methoxy-5-(2-methoxyphenoxy)-2-(2-pyrimidinyl)-4-pyri midinyl]-2-phenylethenesulfoneamide or a salt thereof to the treatment of diseases,

DISCLOSURE OF THE INVENTION

Consequently, the inventors have found that N-[6-methoxy-5-(2-methoxyphenoxy)-2-(2-pyrimidinyl)-4-pyri midinyl]-2-phenylethenesulfoneamide or a salt thereof is effective for the reduction of pains of endothelin-induced diseases, such as cancer (particularly, prostate cancer, breast cancer, ovarian cancer), arthritis, prostatitis, glioma, peripheral artery occlusion, dysmenorrhea, migraine headache, angina, acute cardiac infarction, cerebral infarction, subarachinoid hemorrhage, diabetic nervous disorders, rheumatoid arthritis, glaucoma, gastric ulcer and labor during delivery. Thus, the invention has been achieved.

It is reported that ET-1 induces pain in humans and experimental animals. For example, ET-1 administered to human brachial artery induces ischemic muscular pain (J.Hypertension,8,811–817,1990). Additionally, it is reported that ET-1 significantly enhances the first and second phases of pain due to formalin in the mouse formalin pain model commonly used as a pain model. (Can.J.Physiol.Pharmacol.,75,596–600,1997). In the model, the first phase means pain due to direct stimulation of sensory nerve, while the second phase means pain due to inflammatory secondary reaction (Pain,38,247–352,1989).

As shown in the following Test Example 1, The effective component of the invention exerted an action to suppress the enhancement of pain induced by ET-1 in the mouse formalin pain model.

Further, the inventors have found that N-[6-methoxy-5-(2-methoxyphenoxy)-2-(2-pyrimidinyl)-4-pyri midinyl]-2-phenylethenesulfoneamide or a salt thereof is effective for the amelioration of osteogenic disorders and/or the reduction of pain involved in osteogenesis. Thus, the invention has been achieved.

Because bisphosphonates with an action to suppress osteoclast and thereby ameliorate bone metabolism have an effect to ameliorate bone pain involved in the bone metastasis of breast cancer, the amelioration of long-term bone disorders is believed to lead to the amelioration of bone pain. Unlike bread cancer patients with bone metastasis, osteogenic disorders due to bone metastasis are observed in patients with prostate cancer (Semin.,Oncol.,21,630–656, 1996), and drugs with an action on osteoblast to thereby ameliorate bone metabolism probably have an effect to ameliorate bone pain involved in the bone metastasis of prostate cancer.

It is reported that ET-1 exerts actions to increase intracellular $Ca^{2+}$ concentration and DNA synthesis and to reduce ALP activity through ETA receptors in MC3T3-E1, mouse osteoblast-like cells, and osteoblast primarily cultured from a rat calvaria (Am.J.Physiol.,257,E797–E803,1989/ Biochem.Biophys.Res.Commun.,170(3),998–1005,1990/ Bone,21(2),143–146,1997).

As shown in the following Test Example 2, The effective component of the invention exerted an action to suppress the ET-1-induced cell response reactions of the MC3T3-E1, mouse osteoblast-like cells.

Further, the inventors have found that N-[6-methoxy-5-(2-methoxyphenoxy)-2-(2-pyrimidinyl)-4-pyri midinyl]-2-phenylethenesulfoneamide or a salt thereof is effective for the amelioration of osteogenic disorders due to the bone metastasis of prostate cancer and/or the reduction of pain involved in the bone metastasis of prostate cancer. Thus, the invention has been achieved.

It is reported that a human prostate cancer cell line has a potency to generate ET-1 (Nat.Med.,1(9),944–949,1995) and the growth potency is exerted through ETA receptors (Cancer Res. ,56,663–668,1996) and that the plasma ET-1 concentration in prostate cancer patients with bone metastasis is elevated, compared with the ET-1 concentration in prostate cancer patients without bone metastasis (Nat.Med., 1(9),944–949,1995). Taking account of these reports together with the results of Test Examples 1 and 2, the effective component of the invention is believed to be particularly effective for the amelioration of osteogenic disorders due to the bone metastasis in prostate cancer patients and/or the reduction of pain involved in the bone metastasis of prostate cancer patients. Additionally, as shown in the following Test Example 5, the effective component of the invention reduced pain score and use of analgesics in prostate cancer patients, and decreased bone metabolism markers in prostate cancer patients.

Further, the inventors have found that N-[6-methoxy-5-(2-methoxyphenoxy)-2-(2-pyrimidinyl)-4-pyri midinyl]-2-phenylethenesulfoneamide or a salt thereof is effective for the suppression of the growth of the cancer cell of prostate cancer. Thus, the invention has been achieved.

As shown in the following Test Example 3 and 4, The effective component of the invention suppressed cell growth of hormone-refractory human prostate cancer cell induced by ET-1.

Further, the inventors have found that N-[6-methoxy-5-(2- methoxyphenoxy)-2-(2-pyrimidinyl)-4-pyri midinyl]-2-phenylethenesulfoneamide or a salt thereof is effective for the suppression of the progress of prostate cancer. Thus, the invention has been achieved.

As shown in the following Test Example 5, The effective component of the invention stabilized or decreased Prostate cancer marker PSA in prostate cancer patients.

In other words, the invention relates to a pharmaceutical composition for reducing pain in endothelin-induced diseases, such as cancer (particularly, prostate cancer, breast cancer, ovarian cancer), arthritis, prostatitis, glioma, peripheral artery occlusion, dysmenorrhea, migraine headache, angina, acute cardiac infarction, cerebral infarction, subarachinoid hemorrhage, diabetic nervous disorders, rheumatoid arthritis, glaucoma, gastric ulcer and labor during delivery; a pharmaceutical composition for ameliorating osteogenic disorders; and/or a pharmaceutical composition for reducing pain involved in osteogenesis, particularly a pharmaceutical composition for ameliorating osteogenic disorders due to the bone metastasis of prostate cancer; and/or a pharmaceutical composition for reducing pain involved in the bone metastasis of prostate cancer, the aforementioned compositions containing N-[6-methoxy-5-(2-methoxyphenoxy)-2-(2-pyrimidinyl)-4-pyri midinyl]-2-phenylethenesulfoneamide or a pharmaceutically acceptable salt thereof as the effective components.

Additionally, the invention relates to the use of N-[6-methoxy-5-(2-methoxyphenoxy)-2-(2-pyrimidinyl)-4-pyri midinyl]-2-phenylethenesulfoneamide or a pharmaceutically acceptable salt thereof for the manufacture of a medicament for reducing pain of endothelin-induced diseases such as prostate cancer; a medicament for ameliorating osteogenic disorders; and/or a medicament for reducing pain involved in osteogenesis, particularly a medicament for ameliorating osteogenic disorders due to the bone metastasis of prostate cancer: and/or a medicament for reducing pain involved in the bone metastasis of prostate cancer.

Additionally, the invention relates to a method for reducing pain of endothelin-induced diseases such as prostate cancer and/or pain involved in osteogenesis, particularly pain involved in the bone metastasis of prostate cancer, comprising administering a therapeutically effective dose of N-[6-methoxy-5-(2-methoxyphenoxy)-2-(2-pyrimidinyl)-4-pyri midinyl]-2-phenylethenesulfoneamide or a pharmaceutically acceptable salt thereof to such patients. Still additionally, the invention relates to a method for ameliorating osteogenic disorders, particularly osteogenic disorders due to the bone metastasis of prostate cancer, comprising administering a therapeutically effective dose of N-[6-methoxy-5-(2-methoxyphenoxy)-2-(2-pyrimidinyl)-4-pyri midinyl]-2-phenylethenesulfoneamide or a pharmaceutically acceptable salt thereof to such patients.

The invention relates to a pharmaceutical composition for suppressing the growth of the cancer cell of prostate cancer and/or a pharmaceutical composition for suppressing the progress of prostate cancer, the compositions containing N-[6-methoxy-5-(2-methoxyphenoxy)-2-(2-pyrimidinyl)-4-pyri midinyl]-2-phenylethenesulfoneamide or a pharmaceutically acceptable salt thereof as the effective components.

Additionally, the invention relates to the use of N-[6-methoxy-5-(2-methoxyphenoxy)-2-(2-pyrimidinyl)-4-pyri midinyl]-2-phenylethenesulfoneamide or a pharmaceutically acceptable salt thereof for the manufacture of a medicament for suppressing the growth of the cancer cell of prostate cancer and/or a medicament for suppressing the progress of prostate cancer.

Further, the invention relates to a method for suppressing the growth of the cancer cell of prostate cancer, comprising administering a therapeutically effective dose of N-[6-methoxy-5-(2-methoxyphenoxy)-2-(2-pyrimidinyl)-4-pyri midinyl]-2-phenylethenesulfoneamide or a pharmaceutically acceptable salt thereof to such patients. Furthermore, the invention relates to a method for suppressing the progress of prostate cancer, comprising administering a therapeutically effective dose of N-[6-methoxy-5-(2-methoxyphenoxy)-2-(2-pyrimidinyl)-4-pyri midinyl]-2-phenylethenesulfoneamide or a pharmaceutically acceptable salt thereof to such patients.

Because The effective component of the invention is particularly excellent in terms of oral absorptivity, the compound can be modified into an excellent oral therapeutic agent. As shown in the following Test Example 6. the plasma concentration thereof when orally administered to humans at a dose ½-fold that of ABT-627[1-(N,N-dibutylcarbamoylmethyl)-2(R)-(4-methoxyphenyl)-4(S)-(3, 4-methylenedioxyphenyl)pyrrolidine-3(R)-carboxylic acid] as a known $ET_A$ receptor antagonist is prominently great with AUC of about 18-fold.

The invention is described in more detail hereinbelow.

The effective component of the inventive pharmaceutical composition is N-[6-methoxy-5-(2-methoxyphenoxy)-2-(2-pyrimidinyl)-4-pyri midinyl]-2-phenylethenesulfoneamide or a pharmaceutically acceptable salt thereof. Such salt includes the salt described in the International Patent Publication No. 97/22595 and its specific examples are acid addition salt such as a salt with inorganic acid (for example, hydrochloric acid, hydrobromic acid, hydroiodic acid, sulfuric acid, nitric acid and phosphoric acid) or organic acid (for example, formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid) and a salt with base such as inorganic base (for example, sodium, potassium, magnesium, calcium and aluminum) and organic base (for example, methylamine, ethylamine, ethanolamine, lysine and ornithine) as well as ammonium salt. Particularly preferable is the potassium salt thereof.

The effective component of the invention includes all of mixtures of various isomers thereof and isolated various isomers thereof, hydrated products thereof and solvated products thereof. Additionally, the inventive effective component is sometimes of crystal polymorphism, so the inventive effective component includes all the crystals thereof.

These compounds are readily available by the production method described in the International Patent Publication No. 97/22595 or according to the production method.

The drug of the invention can be prepared as oral solid dosage form, oral liquid dosage form or injection, by using organic or inorganic carriers, excipients and other additives suitable for oral or parenteral administration, according to routine methods. Owing to the great oral absorptivity of the effective component of the invention, the drug of the invention is suitable for oral dosage form. The most preferable is an oral solid dosage form, which can be readily incorporated by patients by themselves and are convenient for storage and transfer.

The oral solid dosage form includes tablet, powder, fine particle, granule, capsule, pill and sustained-release type. In such solid dosage forms, one or more active substances are mixed with at least one inactive diluent, for example lactose, mannitol, glucose, micro-fine cellulose, starch, cornstarch, polyvinylpyrrolidone and metasilicate aluminate magnesium. According to routine methods, the composition may satisfactorily contain additives other than inactive diluents, including for example binders such as hydroxypropyl cellulose and hydroxypropylmethyl cellulose (HPMC); lubricants such as magnesium stearate, polyethylene glycol, starch and talc; disintegrators such as fibrinogen calcium glycolate and cermellose calcium; stabilizers such as lactose; dissolution auxiliary agents such as glutamic acid or aspartic acid; plasticizers such as polyethylene glycol; and colorants such as titanium oxide, talc and yellow ferric oxide. If necessary, the resulting tablet or pill may satisfactorily be coated with sugar coating or films comprising substances solubilizable in stomach or intestine, such as sucrose, gelatin, agar, pectin, hydroxypropyl cellulose and hydroxypropylmethyl cellulose phthalate.

The oral liquid dosage form includes pharmaceutically acceptable emulsions, solutions, suspensions, syrups and elixirs and contains inactive diluents for general use, for example distilled water and ethanol. Other than inactive diluents, the composition may satisfactorily contain auxiliary agents such as moisturizers and suspending agents, sweeteners, flavor, fragrance, and preservatives.

Injections for intravenous, intra-muscular and subcutaneous injection include sterile aqueous or non-aqueous solutions, suspensions and emulsions. The diluents for the aqueous solutions and suspensions include for example distilled water for injections and physiological saline. The diluents for the non-aqueous solutions and suspensions include for example propylene glycol, polyethylene glycol and vegetable oils such as olive oil, alcohols such as ethanol and polysorbate 80. Such composition may additionally contain auxiliary agents such as preservatives, moisturizers, dispersants, stabilizers (for example, lactose), and dissolution auxiliary agents (for example, glutamic acid, aspartic acid). These are sterilized by filtration through bacteria trapping filters or blending with sterilizing agents or under irradiation. These may satisfactorily be used to produce sterile solid compositions, which are dissolved in sterile water or sterile solvents for injections prior to use, and are then used.

The dose of the compound as the effective component of the invention is appropriately determined, depending on each case, taking account of dosage route, diseased conditions, and the age and sex of a dosing subject, but for general administration, the dose of the effective component is about 0.1 to 500 mg/day, preferably 1 to 250 mg/day, per one adult, which is then administered in two-dividend portions.

Herein, the inventive drug can be used in combination with other pain reducing agents, simultaneously or separately in terms of dosing time. For cancerous pain due to prostate cancer and breast cancer, for example, the pain reducing agents include strong opioid analgesics such as morphine for use in the WHO therapeutic mode of cancerous pain, weak opioid analgesics such as pentazocine and buprenorphine, and non-steroidal anti-inflammatory analgesics such as indometacin and ibuprofen.

The inventive drug can be used in combination with other drugs for the therapy of endothelin-induced diseases, simultaneously or separately in terms of dosing time. Therapeutic agents of prostate cancer, which can be used in combination with the inventive drug, include anti-malignant tumor agents such as ifosfamide, tegafur•uracil, estrogen such as ethynylestradiol, adrenal cortex hormones such as hydrocortisone, prednisolone and bemethazone, progesterone such as chloropromazine acetate, LH-RH derivatives such as leuprorelin acetate, LH-RH agonists such as goserelin acetate. anti-malignant tumor platinum complex compounds such as cisplatin, anti-androgen agents such as flutamide, therapeutic agents of prostate cancer, such as fosfestrol and sodium phosphate estramustine, and anti-tumor antibiotics such as peplomycin sulfate.

BRIEF DESCRIPTION OF THE DRAWINGS

FIG. 1 depicts the ET-1-induced enhancement of formalin-induced pain (A: first phase; B: second phase; C: edema);

FIG. 2 depicts the suppressive effects of Compound 1 on the ET-1-induced enhancements of formalin-induced pain (A: first phase; B; second phase; C: edema);

BEST MODE FOR CARRYING OUT THE INVENTION

Figure 3:
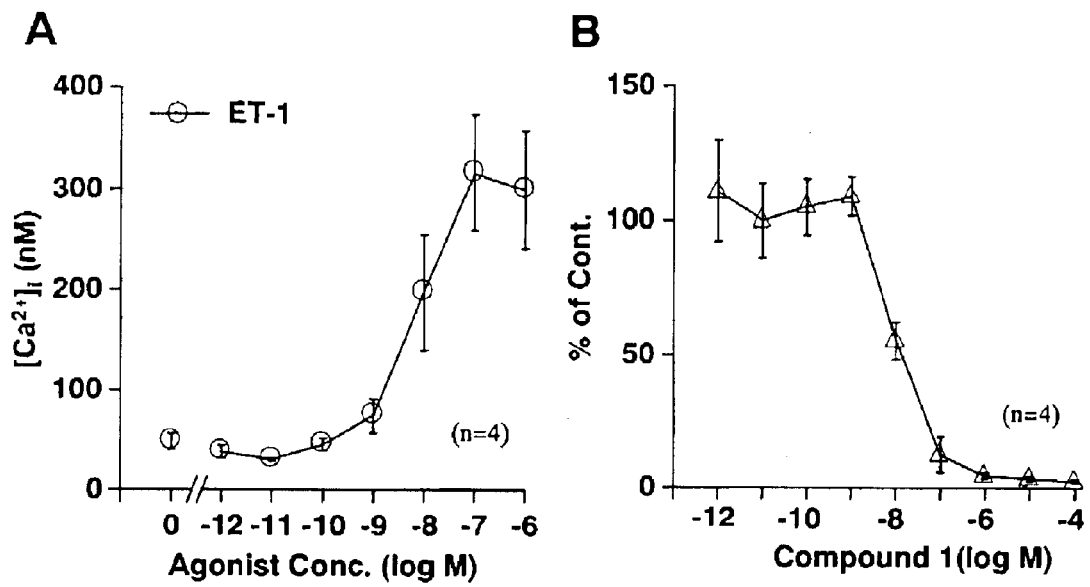
FIG. 3 depicts the suppressive effect of Compound I on the increase of ET-1-induced intracellular $Ca^{2+}$ concentration in MC3T3-E1, mouse osteoblast-like cells.

The invention will be described in more detail hereinbelow with reference to Examples and Test Examples, but the invention is not limited to these Examples and the like. The Compound 1 used in the following Examples and the like means N-[6-methoxy-5-(2-methoxyphenoxy)-2-(2-pyrimidinyl)-4-pyrimidinyl]-2-phenylethenesulfoneamide•potassium salt.

EXAMPLE 1

Capsules

TABLE 1

| Component name | 2 mg Capsule | 10 mg Capsule | 20 mg Capsule |
|---|---|---|---|
| Compound 1 | 2.0 mg | 10 mg | 20.0 mg |
| Lactose | 298.0 mg | 290.0 mg | 280.0 mg |
| Total | 300.0 mg | 300.0 mg | 300.0 mg |

The components were mixed together and filled in capsules, to prepare capsules.

TEST EXAMPLE 1

Suppressive effects of Compound 1 to the enhancement of pain responses induced by ET-1 in mouse formalin-induced pain model
(Method)
1. Animal Used
Male ICR mice (age of 5 weeks; Nippon SLC) were used in these experiments.
2. Measurement of Pain Responses
The mice were placed in a cage for observation, to acclimate the mice to the environment for 5 minutes or longer; then, physiological saline of 20 µl was subcutaneously injected to the mouse left hind paws, while 0.7% formalin-containing physiological saline of 20 µl was subcutaneously injected to the mouse right hind paws. The duration of licking and biting reactions emerging immediately thereafter was counted every 5 minutes, for 40 minutes. After the termination of the counting, both the ankles were amputated and weighed. The reaction time immediately after formalin injection to 5 minutes later was defined as first phase; and the 30 minutes reaction time from 10 minutes after injection until 40 minutes later was defined in total as second phase, which were used as the indices of pain. Additionally, the edema calculated on the basis of the right foot weight minus the left foot weight (in mg) was used as an index of inflammatory reaction. Additionally, in all cases the licking reaction time was counted between 10:00 and 18:00.

3. Test Drugs 0.7% formalin-containing physiological saline containing ET-1 at doses of 3, 10 and 30 pmol/paw was subcutaneously injected in the right hind paws to examine the action of ET-1 to enhance formalin-induced pain and edema.

Compound 1 (0.3 to 3 mg/kg) was orally administered at a dose of 1 ml/100 g. Sixty minutes after oral administration, 0.7% formalin-containing physiological saline containing ET-1 (10 pmol/paw) was subcutaneously injected in the right hind paws, to examine the effect of the Compound 1 on the ET-1-induced enhancements of formalin-induced pain and edema.

4. Statistic Analysis

The results are shown in the form of mean±standard error. The significant difference between two groups was calculated the p-value by Students unpaired t-test. The significant difference between groups was analyzed by one-way analysis of variance, to calculate the p-values by the Dunnett's multiple range test. The p-value below 5% was defined as statistically significant.

(Results)

1. ET-1-induced Enhancement of Formalin-induced Pain and Edema 0.7% formalin solution was subcutaneously injected in the mouse hind paws: then, bi-phase pain responses were observed. Transient pain response (licking and biting reactions; first phase) emerging within 5 minutes immediately after injection was observed, along with sustained pain response (second phase) with a peak around 20 minutes after injection of the formalin solution (FIGS. 1A and 1B). Additionally, edema was induced on the hind legs through the injection of the 0.7% formalin solution (FIG. 1C).

Simultaneous administration of ET-1 (3, 10 and 30 pmol/paw) together with the formalin solution significantly enhanced the first phase, second phase and edema in a dose-dependent manner (FIGS. 1A, 1B and 1C).

2. The Effects of Test Drug on the ET-1-induced Enhancements of Formalin-induced Pain Compound 1 (0.3, 1 and 3 mg/kg, p.o.) significantly suppressed the ET-1 (10 pmol/paw)-induced enhancements of formalin-induced pain (first phase, second phase) and edema (FIGS. 2A, 2B and 2C).

TEST EXAMPLE 2

Test of inhibition of ET-1-induced cell growth of MC3T3-E1, osteoblast-like cells (Method)

1. Cell Used

MC3T3-E1, mouse osteoblast-like cells, was used in these experiments (Journal of Cell Biology,96(1),191–198,1983).

2. Measurement of Intracellular $Ca^{2+}$ Concentration

The cell was cultured in a cell disk (of a 13.5-mm diameter) until the cell reached confluency; thereafter, the cell was then cultured in the absence of serum, for about 12 hours or longer and used for this experiment. Fura2-AM (4 $\mu$M) was added to the cell in the Hank's balanced salt solution (HBSS) (140 mM NaCl, 4 MM KCl, 1 mM $K_2HPO_4$, 1 mM $MgCl_2$, 1 mM $CaCl_2$, 10 mM glucose and 20 mM Hepes, pH-7.4) and incubated at 37° C. for one hour. The cell disk was fixed in a quartz cell placing therein HBSS; the quartz cell was fixed in an intracellular $Ca^{2+}$ assay unit (CAF-110). The experiment was started when the cell reached a constant state under agitation conditions with a stirrer at 37° C. Intracellular $Ca^{2+}$ concentration was estimated by measuring and detecting the ratio of fluorescence intensities at 500 nm with excitation wave lengths of 340/380 nm and calculating intracellular $Ca^{2+}$ concentration using designated formula (J.Biol.Chem.,260,3440–3450, 1985).

3. Measurement of DNA Synthesis Level

As DNA synthesis level, the incorporation of [$^3$H]-labeled thymidine was assayed. The cells were seeded at a density of $1.5 \times 10^4$ cells/well in a 96-well plate using 0.2% FCS culture medium and cultured for 2 days. Subsequently, vehicle or ET-1 was added to the plate and cultured for 24 hours. Continuously, [$^3$H-methyl]-thymidine was added at 0.5 $\mu$Ci/well to the culture and pulse-labeling performed for 6 hours. Continuously, SDS solution to a final concentration of 0.2% was added for solubilization of the cell, and after solubilization the radioactivity of [$^3$H-methyl]-thymidine used for DNA synthesis was counted with a liquid scintillation counter. As a control, the count of a culture to which the vehicle was added was defined 100%, thus the percentage increase of DNA synthesis was calculated.

4. Cell Number Counting Assay

Cell number was counted by using a reagent solution of a cell counting kit (DOJINDO). The cells were seeded at a density of $1.0 \times 10^4$ cells/well in a 24-well plate using 0.5% FCS culture medium and cultured for one day. Subsequently, vehicle or ET-1 was added to the plate and cultured for 72 hours. Continuously, a reagent solution was added at 100 $\mu$l/well to the culture and incubated at 37° C. for 3 hours. After this reaction, 200-$\mu$l portions were transferred from the individual wells of the 24-well plate to a 96-well plate, to measure the absorbance (at a wave length of 405 nm and a reference wave length of 650 nm) with a plate reader. As a control, the count of a culture to which the vehicle was added was defined 100%, thus the percentage increase of cell number was calculated.

5. Test Drugs

In each experiments, ET-1 and Compound 1 were within the concentration ranges of $10^{-13}$ to $10^{-6}$ M and $10^{-12}$ to $10^{-4}$ M, respectively, as the final concentrations thereof (all at 10-fold dilution series). Compound 1 was added about 2 minutes before the addition of ET-1 for the assay of intracellular $Ca^{2+}$ concentration and about 2 hr before the addition of ET-1 in other experiments.

6. Statistic Analysis

The results are shown in the form of mean±standard error. The significant difference between groups was analyzed by one-way analysis of variance, to calculate the p-values by the Dunnett's multiple range test. The p-value below 5% was defined as statistically significant. At each experiment, the $EC_{50}$ value of ET-1 and the $IC_{50}$ value of the Compound 1 were calculated by the Logistic regression analysis.

(Results)

1. The inhibitory effect of Compound 1 on ET-1-induced increasing in intracellular $Ca^{2+}$ concentration in MC3T3-E1 ET-1 ($10^{-12}$ to $10^{-6}$ M) increased the intracellular $Ca^{2+}$ concentration in the MC3T3-E1, mouse osteoblast-like cell in a concentration-dependent manner (FIG. 3A). The EC$_{50}$ value of ET-1 was 7.39×10$^{-9}$ M. Compound 1 (10$^{-12}$ to 10$^{-4}$ M) inhibited the ET-1 (10$^{-8}$ M)-induced increasing in the intracellular Ca$^{2+}$ concentration in a concentration-dependent manner (FIG. 3B). The IC$_{50}$ value of Compound 1 was 1.02×10$^{-8}$ M.

2. The inhibitory effect of Compound 1 on ET-1-induced increasing in cell growth of MC3T3-E1

Figure 4:
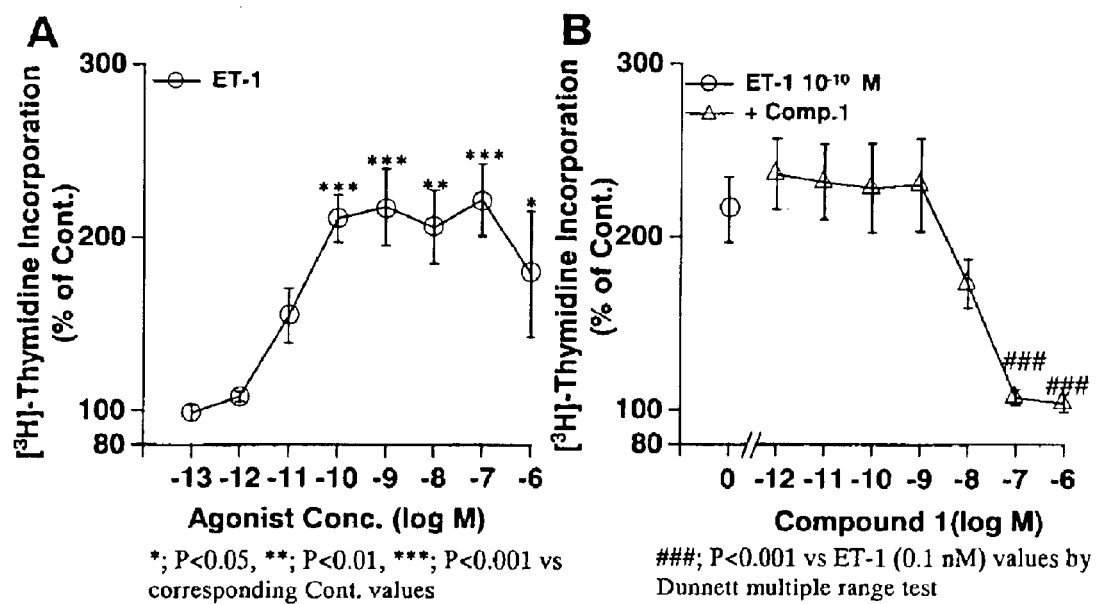
FIG. 4 depicts the suppressive effect of Compound 1 on the increase of ET-1-induced cell growth ($[^3H]$-thymidine incorporation) in MC3T3-E1, mouse osteoblast-like cells.

ET-1 (10$^{-13}$ to 10$^{-6}$ M) significantly increased the incorporation of [$^3$H]-thymidine to increase DNA synthesis in the MC3T3-E1, mouse osteoblast-like cells, in a concentration-dependent manner (FIG. 4A). The EC$_{50}$ value of ET-1 was 9.84×10$^{-12}$ M. Compound 1 (10$^{-12}$ to 10$^{-6}$ M) inhibited the ET-1 (10$^{-10}$ M)-induced increasing in the incorporation of [$^3$H]-thymidine in a concentration-dependent manner (FIG. 4B). The IC$_{50}$ value of Compound 1 was 1.15×10$^{-8}$ M.

Figure 5:
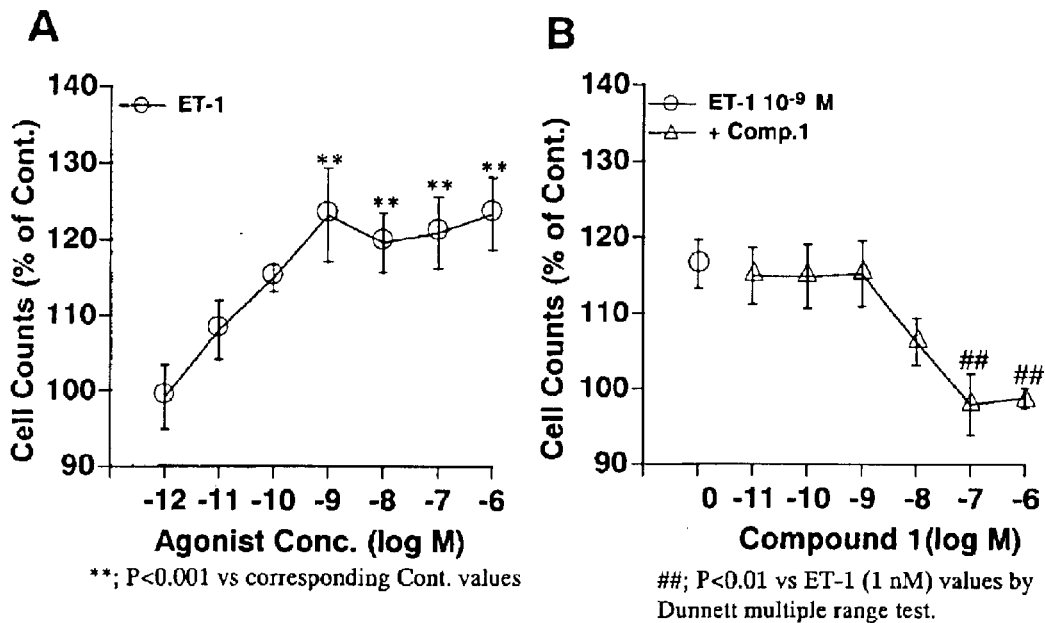
FIG. 5 depicts the suppressive effect of Compound 1 on the increase of ET-1-induced cell growth (cell number) in MC3T3-E1, mouse osteoblast-like cells.

Similarly, ET-1 (10$^{-12}$ to 10$^{-6}$M) significantly increased the cell number of the MC3T3-E1 in a concentration-dependent manner at an experiment to assay cell number with WST-1 (FIG. 5A). The EC$_{50}$ value of ET-1 was 2.20×10$^{-11}$ M. Compound 1 (10$^{-11}$ to 10$^{-6}$ M) inhibited the ET-1 (10$^{-9}$ M)-induced increasing in the cell number in a concentration-dependent manner (FIG. 5B). The IC$_{50}$ value of Compound 1 was 9.54×10$^{-9}$ M.

TEST EXAMPLE 3

Test of inhibition of ET-1-induced cell growth of hormone-refractory human prostate cancer cells (1)
(Method)
1. Cell Used PPC-1, hormone-refractory human prostate cancer cells, was used in these experiments (International Journal of Cancer,44,898–903,1989).

2. Examination of the Effect of ET-1 on the Cell Growth of PPC-1 and Inhibitory Effect of Test Drug Thereon DNA synthesis level was measured as the index of cell growth. As DNA synthesis level, the incorporation of [$^3$H]-labeled thymidine was assayed. The cells were seeded at a density of 1×10$^4$ cells/well in a 96-well plate using no FCS-added culture medium and cultured for 5 days. Subsequently, vehicle or ET-1 was added to the plate and cultured for 24 hours. Continuously, [$^3$H-methyl]-thymidine was added at 0.5 µCi/well to the culture and pulse-labeling performed for 6 hours. Continuously, SDS solution to a final concentration of 0.2% was added for solubilization of the cell, and after solubilization the radioactivity of [$^3$H-methyl]-thymidine used for DNA synthesis was counted with a liquid scintillation counter. As a control, the count of a culture to which the vehicle was added was defined 100%, thus the percentage increase of DNA synthesis was calculated.

3. Test Drugs

In this experiment, ET-1 and Compound 1 were within the concentration ranges of 10$^{-13}$ to 10$^{-6}$ M (10-fold dilution series) and 10$^{-10}$ to 3×10$^{-6}$ M (3-fold dilution series), respectively, as the final concentrations thereof. Compound 1 was added about 2 hr before the addition of ET-1.

4. Statistic Analysis

The results are shown in the form of mean t standard error. The significant difference between groups was analyzed by one-way analysis of variance, and calculated the p-values by the Dunnett's multiple range test. The p-value below 5% was defined as statistically significant. The IC$_{50}$ value of the Compound 1 were calculated by the Logistic regression analysis.

(Results)

Figure 6:
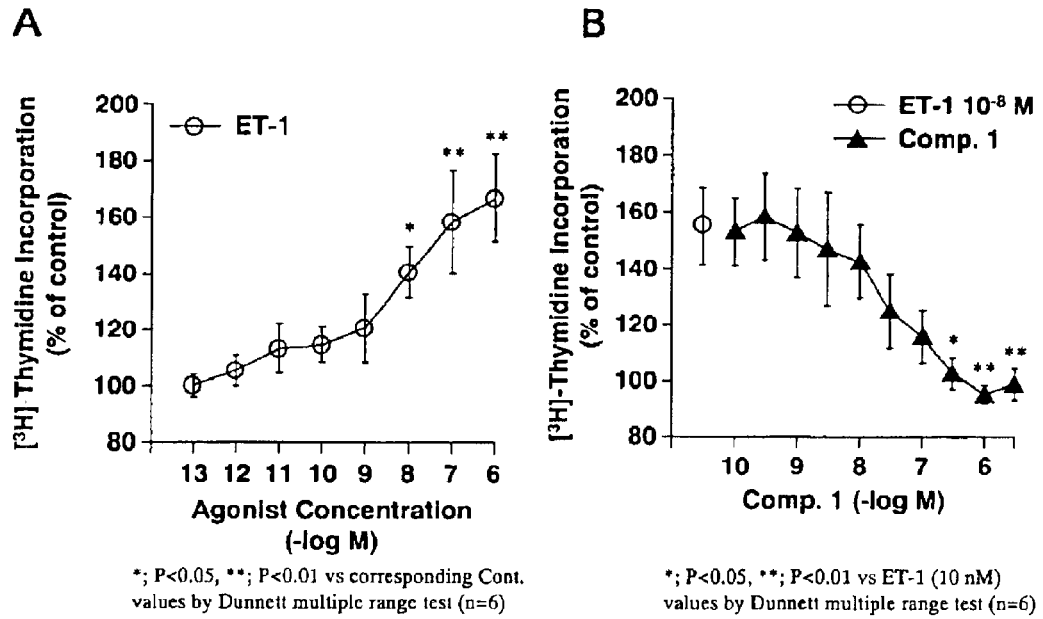
FIG. 6 depicts the suppressive effect of Compound 1 on the increase of ET-1-induced cell growth in PPC-1, hormone-refractory human prostate cancer cells.

As shown in FIG. 6A, ET-1 (10$^{-13}$ to 10$^{-6}$ M) increased the incorporation of [$^3$H]-thymidine in the PPC-1, hormone-refractory human prostate cancer cells, in a concentration-dependent manner, suggesting the exertion of the action to promote cell growth. The effect of ET-1 above 10$^{-8}$ M was statistically significant.

The compound 1 (10$^{-10}$ to 3×10$^{-5}$ M) inhibited the ET-1 (10$^{-8}$ M)-induced promotion of PPC-1 cell growth in a concentration-dependent manner, and the IC$_{50}$ value was 28±9.8 nM (FIG. 6B). The inhibitory effect of the Compound 1 above 3×10$^{-7}$ M was statistically significant.

TEST EXAMPLE 4

Test of inhibition of ET-1-induced cell growth of hormone-refractory human prostate cancer cells (2)
(Method)
1. Cell Used PPC-1, hormone-refractory human prostate cancer cells, was used in these experiments(International Journal of Cancer,44,898–903,1989).

2. Examination of the Effect of ET-1 on the Cell Growth and Inhibitory Effect of Test Drug Thereon Cell number was counted by using a reagent solution of a alamar blue. The cells were seeded at 2×10$^4$ cells/well in a 24-well plate, after adhesion, the culture media were exchanged to culture media with no FCS-added, and further cultured for another 24 hours. Thereafter, vehicle or ET-1 (10$^{-11}$ to 10$^{-6}$ M) was added, and cultured for 96 hours. The final volume of the culture medium was 500 µl. Alamar blue of 50 µl was added to the culture, and incubated for 4 hours. After reaction, 100 µl portions collected from the individual wells of the 24-well plate were then transferred to a 96-well plate, and measured the absorbance (at a wave length of 405 nm and a reference wave length of 650 nm) with a plate reader. As a control, the count of a culture to which the vehicle was added was defined 100%, thus the percentage increase of cell number was calculated. The inhibitory effect of the compound was examined by adding the Compound 1 to a final concentration of 10$^{-9}$ to 10$^{-5}$ M, 30 minutes prior to the addition of ET-1 at 10$^{-7}$ M.

At the experiment, the culture medium was exchanged to a culture medium to which ET-1 was contained, 48 hours after stimulation, because the degradation of ET-1 was possible.

(Results)

As shown in Table 2, the cell growth induced by ET-1 was observed in PPC-1, starting from 10$^{-11}$ M.

TABLE 2

| ET-1 (M) | Cell growth (%) |
| --- | --- |
| 0 (control) | 100.0 |
| 10$^{-11}$ | 119.6 |
| 10$^{-10}$ | 122.3 |
| 10$^{-9}$ | 124.0 |
| 10$^{-8}$ | 115.3 |
| 10$^{-7}$ | 119.3 |

(n = 7)

Additionally, as shown in Table 3, the Compound 1 inhibited the cell growth induced by 10$^{-7}$ M ET-1 in PPC-1, starting from 10$^{-6}$ M.

TABLE 3

| ET-1 | Compound 1 | Cell growth (%) |
| --- | --- | --- |
| — | — | 100.0 |
| 10$^{-7}$M | 0 | 110.5 |

TABLE 3-continued

| ET-1 | Compound 1 | Cell growth (%) |
|---|---|---|
|  | $10^{-6}$M | 99.2 |
|  | $10^{-5}$M | 98.1 |

(n = 7)

TEST EXAMPLE 5

Clinical Study in Prostate Cancer Patients (Method)

A clinical study was carried out under the following conditions using the patients suffering from prostate cancer.

Subjects: eighteen patients of at least 45 years of age with prostate cancer(stage D2) who are hormone-refractory or have relapsed after anti-androgen therapy.

Test drug: Compound 1

Strength: 2,10 and 40 mg tablets

Dosage: 2,4,10,20,60,120and 240 mg/day-dose frequency was once daily ot twice daily Duration of treatment: four weeks (28 days)

Parameters for evalution: Evaluations and measurements were made for the following items before and after the administration.

(1) Prostate specific antigen (PSA)
(2) Born metabolism markers (bone alkaline phosphatase or ratio of deoxypyridinoline/creatinine)
(3) Bone pain (change of visual analogue scale(VAS)/use of analgesics)

(Results)

The Compound 1 is effective in improving each observed items, starting at a dose of 2 mg/day. The Compound 1 improved pain score VAS in nine (out of eighteen) patients. The Compound 1 reduced analgesics in four (out of eighteen) patients. The Compound 1 improved prostate cancer marker PSA in ten patients and stabilized in two other patients. The Compound 1 decreased bone specific alkaline phosphatase in eleven (out of eighteen) patients and Improved the ratio of deoxypyridinoline/creatinine in fourteen (out of eighteen) patients.

TEST EXAMPLE 6

Plasma Concentration when Orally Administered to Humans (Method)

For the purpose of the assessment of the pharmacokinetics, tolerance and safety of Compound 1 when orally administered, the Compound 1 was administered at a single dose of 10 mg to 3 subjects of progressive prostate cancer patients after prostatectomy. So as to assay the plasma concentration of intact Compound 1, blood of 6 ml was collected in a lithium heparin-containing polyethylene tube, prior to administration and at individual times of 30 minutes, one hour, 1.5 hour, 2 hours, 3 hours, 4 hours, 6 hours, 8 hours, 12 hours, 24 hours, 36hours and 48hours after administration, followed by immediate centrifugation (4° C., 10 minutes, 3500 rpm), to recover the plasma. The plasma samples were stored under freezing at −70° C. until the concentration was assayed. The plasma concentration was assayed by the LC-MS/MS method.

(Results)

As shown in Table 4, the Cmax and AUC of the Compound 1 when orally administered at a single dose of 10 mg were at higher values about 11-fold and about 18-fold, respectively, those of ABT-627 administered at 20 mg.

TABLE 4

|  | AUC (ng · h/ml) | Cmax (ng/ml) | T max (h) | T ½ (h) |
|---|---|---|---|---|
| Compound 1 10 mg | 14700 | 1000 | 2 | 13 |
| ABT-627 20 mg* | 802 | 93.5 | 0.6 | 28.4 |
| Compound 1 (10 mg)/ABT-627 (20 mg) | 18 | 11 |  |  |

*) 6th International Conference on Endothelin, Oct. 10–13, 1999, Abstract No. 219.

The results of the Test Example 1 verify that the Compound 1 is useful as a pain reduction agent for endothelin-induced diseases.

The results of the Test Example 2 verify that the Compound 1 ameliorates osteogenic bone disorders and is useful as an agent to reduce pain involved in osteogenesis.

Additionally in the Test Example 2, it is indicated that ET-1 induces osteoblast-like cell response, starting from a very low concentration of about $1\times10^{-11}$M. In a report concerning the ET-1 generation potencies of human prostate cancer cell lines, ET-1 generation of about several tens pg/ml $10^6$ cells/24 hr is reported (Nat. Med., 1(9), 944–949, 1995). The concentration corresponds to about $1\times10^{-11}$ M. The results of the Test Example 2 indicate evidences strongly suggesting the possibility of ET-1 generated in the prostate cancer cells to form an osteogenic bone disorder. In the Test Example 2, it is shown that the Compound 1 at a low concentration around 10 nM suppresses the osteoblast-like cell response due to ET-1. Therefore, it is strongly suggested that the Compound 1 exerts an amelioration effect of osteogenic bone disorders in prostate cancer patients, for which ET-1 is suggested to be responsible. Taking account of the results of the Test Example 1 together, it is strongly suggested that the Compound 1 is useful as an agent for reducing pain involved in the bone metastasis of prostate cancer.

Additionally, the results of the Test Example 5 support that the Compound 1 is useful as an agent for reducing pain involved in the bone metastasis of prostate cancer.

The results of the Test Examples 3 and 4 verify that the Compound 1 is useful as a suppressive agent of the growth of the hormone-resistant cancer cell of prostate cancer. Additionally, it is strongly suggested that the Compound 1 exerts an effect on the suppression of the progress of prostate cancer.

Additionally, the results of the Test Example 5 also support that the Compound 1 is effective as a suppressive agent of the progress of prostate cancer.

Furthermore, it is indicated in the test Example 6 that the AUC of the Compound 1 at a half dose of ABT-627 is as high as about 18-fold that of ABT-627 approved as a known $ET_A$ receptor antagonist, suggesting that the oral absorptivity and pharmacokinetics of the Compound 1 when orally administered are great. Though, the affinity of the Compound 1 to human $ET_A$ receptor is 0.697 nM(WO97/22595) and similarly that of ABT-627 is 0.48 nM(J.Pharmacol.Exp.Ther.,276,473–481,1996), the Compound 1 is promising as a greater oral therapeutic agent than ABT-627.

Additionally in the Test Example 5, the Compound 1 is effective, starting at a dose of 2 mg, which verifies that the Compound 1 is a great oral therapeutic agent of prostate cancer, because the dose corresponds to ⅕-fold the minimum effective dose of ABT-627, which is reported to be 10 mg(Proceeding of ASCO,19,1314,2000). Thus, it is confirmed that the Compound 1 is a great oral therapeutic agent of prostate cancer.

INDUSTRIAL APPLICABILITY

According to the invention, a great oral therapeutic agent of prostate cancer can be provided, which is effective in clinical practice. In other words, a therapeutic agent for reducing pain in an endothelin-induced disease, such as such as cancer (particularly, prostate cancer, breast cancer), arthritis, prostatitis, glioma, peripheral artery occlusion, dysmenorrhea, migraine headache, angina, acute cardiac infarction, cerebral infarction, subarachinoid hemorrhage, diabetic nervous disorders, rheumatoid arthritis, glaucoma, gastric ulcer and labor during delivery can be provided. Additionally, a therapeutic agent for ameliorating osteogenic disorders and/or a therapeutic agent for reducing pain involved in osteogenesis, particularly a therapeutic agent for reducing pain involved in the bone metastasis of prostate cancer and/or a therapeutic agent for ameliorating osteogenic disorders due to the bone metastasis of prostate cancer can be provided. Further, a therapeutic agent for suppressing the growth of the cancer cell of prostate cancer and/or a therapeutic agent for suppressing the progress of prostate cancer can be provided.

What is claimed is:

1. A method for reducing pain of endothelin-induced cancer diseases comprising administering a therapeutically effective dose of N-[6-methoxy-5-(2-methoxyphenoxy)-2-(2-pyrimidinyl)4-pyrimidinyl]-2-phenylethenesulfoneamide or a pharmaceutically acceptable salt thereof to a cancer patient in need thereof.

2. The method according to claim 1, wherein the endothelin-induced cancer disease is prostate cancer.

3. A method for reducing pain involved in bone metastasis of prostate cancer, comprising administering a therapeutically effective dose of N-[6-methoxy-5-(2-methoxyphenoxy)-2-(2-pyrimidinyl)-4-pyrimidinyl]-2-phenylethenesulfoneamide or a pharmaceutically acceptable salt thereof to a prostate cancer patient in need thereof.

4. A method for ameliorating osteogenic disorders due to the bone metastasis of prostate cancer, comprising administering a therapeutically effective dose of N-[6-methoxy-5-(2-methoxyphenoxy)-2-(2-pyrimidinyl)-4-pyrimidinyl]-2-phenylethenesulfoneamide or a pharmaceutically acceptable salt thereof to a prostate cancer patient in need thereof.

5. A method for suppressing the growth of a prostate cancer cell, comprising administering a therapeutically effective dose of N-[6-methoxy-5-(2-methoxyphenoxy)-2-(2-pyrimidinyl)-4-pyrimidinyl]-2-phenylethenesulfoneamide or a pharmaceutically acceptable salt thereof to a prostate cancer patient in need thereof.

6. The method according to claim 5, wherein the prostate cancer is a non-hormone dependent form of prostate cancer.

7. A method for suppressing the progress of prostate cancer, comprising administering a therapeutically effective dose of N-[6-methoxy-5-(2-methoxyphenoxy)-2-(2-pyrimidinyl)-4-pyrimidinyl]-2-phenylethenesulfoneamide or a pharmaceutically acceptable salt thereof to a prostate cancer patient in need thereof.

* * * * *